(12) United States Patent
Choi et al.

(10) Patent No.: US 11,471,546 B2
(45) Date of Patent: Oct. 18, 2022

(54) LIGHTING DEVICE

(71) Applicant: Seoul Viosys Co., Ltd., Ansan-si (KR)

(72) Inventors: Jae Young Choi, Ansan-si (KR); Kyu Won Han, Ansan-si (KR); Seong Tae Jang, Ansan-si (KR); Sang Wook Jung, Ansan-si (KR); Woong Ki Jeong, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 0 days.

(21) Appl. No.: 16/633,449

(22) PCT Filed: Jul. 20, 2018

(86) PCT No.: PCT/KR2018/008222
§ 371 (c)(1),
(2) Date: Jan. 23, 2020

(87) PCT Pub. No.: WO2019/022441
PCT Pub. Date: Jan. 31, 2019

(65) Prior Publication Data
US 2020/0230271 A1 Jul. 23, 2020

(30) Foreign Application Priority Data
Jul. 27, 2017 (KR) .......................... 10-2017-0095693

(51) Int. Cl.
*F21V 9/45* (2018.01)
*A61L 2/10* (2006.01)
(Continued)

(52) U.S. Cl.
CPC .................................... *A61L 2/10* (2013.01);
*F21V 1/20* (2013.01); *F21V 1/22* (2013.01);
*F21V 14/02* (2013.01);
(Continued)

(58) Field of Classification Search
CPC ..... A61L 2/10; F25D 27/00; F25D 2317/0417
See application file for complete search history.

(56) References Cited

U.S. PATENT DOCUMENTS

| 5,595,438 A | 1/1997 | Burd |
| 9,144,617 B2 | 9/2015 | Deng |

(Continued)

FOREIGN PATENT DOCUMENTS

| CN | 101322000 | 12/2008 |
| CN | 103453355 | 12/2013 |

(Continued)

OTHER PUBLICATIONS

International Search Report dated Oct. 29, 2018, in International Patent Application No. PCT/KR2018/008222 (with English Translation).

(Continued)

*Primary Examiner* — Andrew J Coughlin
(74) *Attorney, Agent, or Firm* — H.C. Park & Associates, PLC

(57) ABSTRACT

A lighting device including at least one first light source emitting a visible light, at least one second light source spaced apart from the first light source and emitting a light having a wavelength for sterilization, and a housing, in which the first light source and the second light source are disposed, in which the first light source is disposed outside an area having an angle corresponding to about 50% of a maximum amount of light emitted from the second light source based on a line extending from a center of the second light source along a direction substantially perpendicular to a light emitting surface of the second light source.

24 Claims, 7 Drawing Sheets

(51) Int. Cl.
*F21V 1/20* (2006.01)
*F21V 1/22* (2006.01)
*F21V 14/02* (2006.01)
*F21V 15/01* (2006.01)
*F21V 23/04* (2006.01)
*F21V 33/00* (2006.01)
*F21Y 115/10* (2016.01)

(52) U.S. Cl.
CPC .......... *F21V 15/01* (2013.01); *F21V 23/0464* (2013.01); *F21V 23/0471* (2013.01); *F21V 33/0012* (2013.01); *F21Y 2115/10* (2016.08)

(56) References Cited

U.S. PATENT DOCUMENTS

| | | | |
|---|---|---|---|
| 10,245,337 | B2 | 4/2019 | Park et al. |
| 10,551,032 | B2 | 2/2020 | Hikmet et al. |
| 2007/0247831 | A1* | 10/2007 | Buelow ................ A47F 3/0426 362/92 |
| 2008/0008620 | A1 | 1/2008 | Alexiadis |
| 2009/0323306 | A1* | 12/2009 | Son .......................... F21V 9/38 362/84 |
| 2010/0315810 | A1 | 12/2010 | Tseng |
| 2015/0369455 | A1 | 12/2015 | Nieminen |
| 2016/0136312 | A1 | 5/2016 | Park et al. |
| 2016/0335826 | A1 | 11/2016 | Sano |
| 2017/0175953 | A1 | 6/2017 | Van Boven et al. |
| 2018/0320872 | A1 | 11/2018 | Weeks, Jr. et al. |
| 2019/0224353 | A1 | 7/2019 | Park et al. |

FOREIGN PATENT DOCUMENTS

| | | |
|---|---|---|
| CN | 104822987 | 8/2015 |
| CN | 105351871 | 2/2016 |
| DE | 202010002018 | 5/2010 |
| DE | 102010017573 | 8/2011 |
| DE | 202011101343 | 8/2011 |
| JP | H08-264009 | 10/1996 |
| KR | 10-2013-0078915 | 7/2013 |
| KR | 10-2013-0125436 | 11/2013 |
| KR | 10-1346576 | 1/2014 |
| KR | 10-2015-0024717 | 3/2015 |
| KR | 10-1535242 | 7/2015 |
| KR | 10-2017-0030166 | 3/2017 |
| KR | 10-2017-0062188 | 6/2017 |
| WO | 2007/149585 | 12/2007 |
| WO | 2007/149585 | 11/2008 |
| WO | 2009/148237 | 12/2009 |
| WO | 2014/088298 | 6/2014 |
| WO | 2014/118431 | 8/2014 |
| WO | 2015/121761 | 8/2015 |
| WO | 2017/012829 | 1/2017 |
| WO | 2017/083461 | 5/2017 |

OTHER PUBLICATIONS

Extended European Search Report dated Dec. 21, 2020, corresponding to European Application No. EP18837945.7.
Extended European Search Report dated Apr. 12, 2021, issued in European Patent Application No. 18838095.0.
European Search Report dated May 31, 2021, issued to European Patent Application No. 21171042.1.
Office Action dated Feb. 2, 2022, issued to Korean Patent Application No. 10-2017-0095693.
Office Action dated Feb. 18, 2022, issued to Chinese Patent Application No. 201880035114.

* cited by examiner

LIGHTING DEVICE

CROSS-REFERENCE TO RELATED APPLICATIONS

This application is a National Stage Entry of International Application No. PCT/KR2018/008222, filed on Jul. 20, 2018, and claims priority from and the benefit of Korean Patent Application No. 10-2017-0095693, filed on Jul. 27, 2017, of which is hereby incorporated by reference for all purposes as if fully set forth herein.

BACKGROUND

Field

Exemplary embodiments of the invention relate generally a lighting device to and, more specifically, to a lighting device with a sterilization function.

Discussion of the Background

The kitchen where people spend a lot of time provides a good environment for germs to grow, because the kitchen is generally located indoors, and the temperature and humidity in the kitchen are relatively high. As such, various types of sterilizers may be necessary for cleanliness and a user's health.

The above information disclosed in this Background section is only for understanding of the background of the inventive concepts, and, therefore, it may contain information that does not constitute prior art.

SUMMARY

Lighting devices constructed according to exemplary embodiments of the invention are capable of providing lighting function and superior sterilization function.

Additional features of the inventive concepts will be set forth in the description which follows, and in part will be apparent from the description, or may be learned by practice of the inventive concepts.

A lighting device according to an exemplary embodiment includes at least one first light source emitting a visible light, at least one second light source spaced apart from the first light source and emitting a light having a wavelength for sterilization, and a housing, in which the first light source and the second light source are disposed, in which the first light source is disposed outside an area having an angle corresponding to about 50% of a maximum amount of light emitted from the second light source based on a line extending from a center of the second light source along a direction substantially perpendicular to a light emitting surface of the second light source.

The lighting device may further include a first substrate on which the first light source is mounted and a second substrate on which the second light source is mounted.

The first substrate and the second substrate may be disposed on different planes from each other.

The first substrate and the second substrate may be disposed on the same plane as each other.

The first substrate and the second substrate may be integrally formed without being spaced apart from each other.

The housing may include a bottom portion on which the first light source is disposed and a sidewall portion connected to the bottom portion.

The first light source and the second light source may be disposed at different heights from the bottom portion.

The height of the first light source from the first substrate may be lower than the height of the second light source from the first substrate.

The second light source may be disposed on at least one of the bottom portion and the sidewall portion.

The lighting device may further include a cover unit that is coupled to the sidewall portion to face the bottom portion and covers the first light source.

The cover unit may include a diffusion member to diffuse the light.

The cover unit may cover the second light source.

The cover unit may include at least one of quartz, polymethylmethacrylate, polycarbonate, polyvinylalcohol, polypropylene, and low-density polyethylene.

The cover unit may include an opening defined in an area, in which the second light source is disposed, and the second light source may be exposed to an outside through the opening.

The cover unit and the second substrate may be disposed on the same plane as each other.

The second light source may be rotatable.

The lighting device may further include at least one of an illuminance sensor and a motion sensor which are disposed at one side of the housing.

The lighting device may further include a controller driving a power of the first light source and the second light source and connected to at least one of the illuminance sensor and the motion sensor, and the controller drives the power of the first light source and the second light source depending on a sensing result by at least one of the illuminance sensor and the motion sensor.

The controller may turn off the second light source when the motion sensor senses that a distance between the lighting device and a user reaches a predetermined limit approach distance.

At least one of the first light source and the second light source may be provided in plural.

When the second light source is provided in plural, at least one of the second light sources may emit light having different wavelength from that emitted from the remaining second light sources.

The lighting device may be mounted on a kitchen furniture.

A visible light lighting device according to another exemplary embodiment coupled to a second light source that is configured to emit light having a wavelength for sterilization includes at least one first light source configured to emit a visible light, and a housing at which the first light source is disposed, in which the first light source is disposed outside an area having an angle corresponding to about 50% of a maximum amount of light emitted from the second light source based on a line extending from a center of the second light source along a direction substantially perpendicular to a light emitting surface of the second light source.

A light source according to yet another exemplary embodiment coupled to a visible light lighting device including a first light source configured to emit a visible light, and a housing at which the first light source is disposed includes a coupling unit coupled to the housing, in which the light source is configured to emit light having a wavelength for sterilization, and the light source and the first light source are disposed on different planes from each other.

It is to be understood that both the foregoing general description and the following detailed description are exemplary and explanatory and are intended to provide further explanation of the invention as claimed.

BRIEF DESCRIPTION OF DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
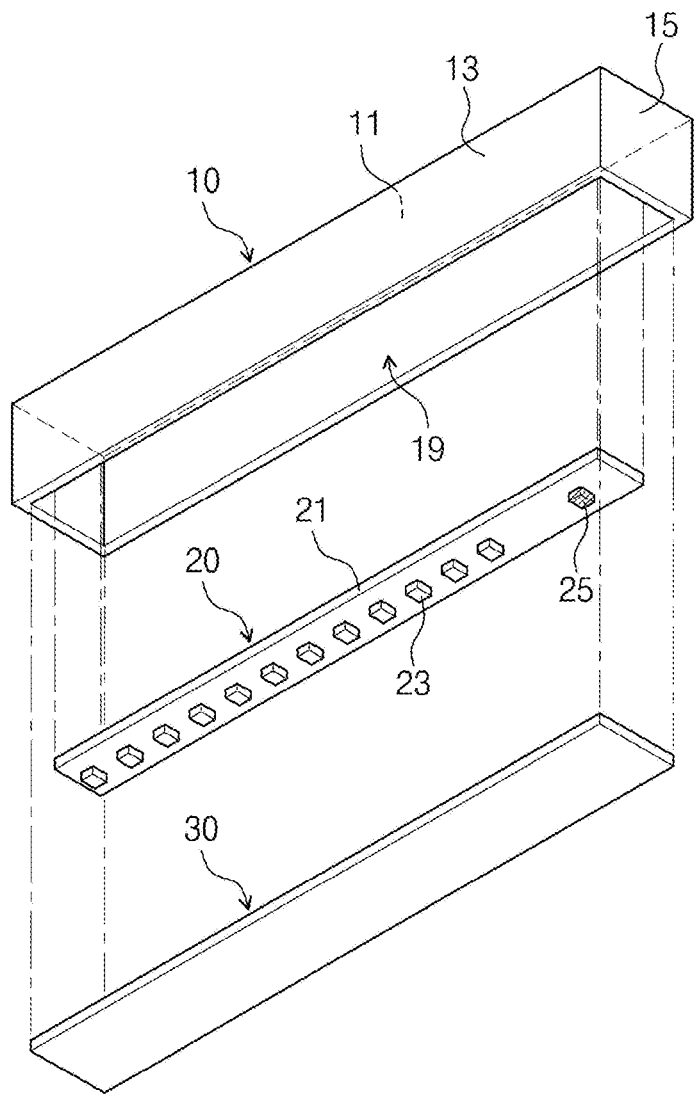
FIG. 1 is an exploded perspective view of a lighting device according to an exemplary embodiment.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

A lighting device according to an exemplary embodiment relates to a lighting device having a sterilization function in addition to a lighting function to illuminate a predetermined area with a light. The lighting device according to an exemplary embodiment may be mounted on a kitchen furniture (e.g., a kitchen sink cabinet). However, the lighting device according to an exemplary embodiment is not for being used only in the kitchen furniture, but also may be employed in various devices. For example, the lighting device according to an exemplary embodiment may be employed in devices that require sterilization and lighting, such as refrigerators for various purposes (e.g., refrigerators for home, warehouse, car, kimchi storage, etc.), sterilizers for various purposes (e.g., sterilizers for cookware, toothbrushes, feeding bottles, shoes, etc.), and a dish washer. Hereinafter, a light device will exemplarily be described as being mounted on the kitchen furniture.

Figure 2:
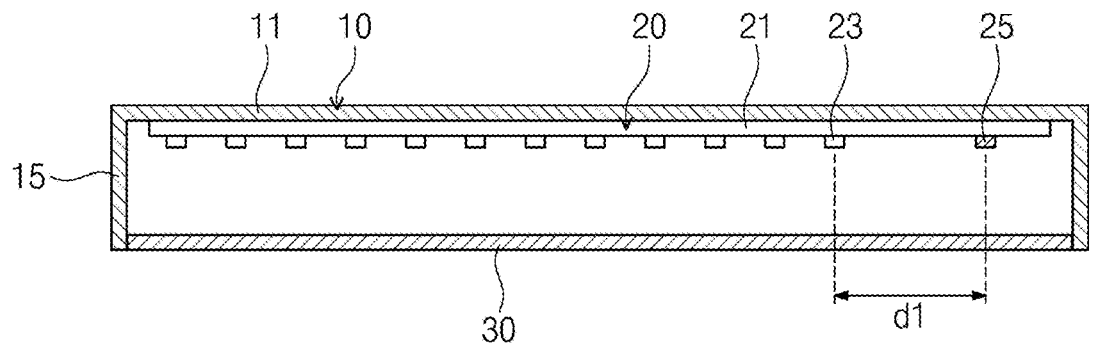
FIG. 2 is a cross-sectional view of the lighting device of FIG. 1 in a longitudinal direction of the lighting device.

FIG. 1 is an exploded perspective view of a lighting device according to an exemplary embodiment. FIG. 2 is a cross-sectional view of the lighting device of FIG. 1 in a longitudinal direction of the lighting device.

Referring to FIGS. 1 and 2, the lighting device according to an exemplary embodiment includes a light source unit 20 emitting light having a predetermined wavelength band, a housing 10 in which the light source unit 20 is disposed, and a cover unit 30 covering one side of the housing 10.

In FIGS. 1 and 2, light emitted from the light source unit 20 travels to a downward direction. As used herein, the emission direction of the light is referred to as the "downward direction", and an opposite direction to the emission direction of light is referred to as an "upward direction". However, the terms indicating the directions are relative terms, and thus, the directions may be changed depending on a specific device to which the lighting device is mounted.

The housing 10 forms an appearance of the lighting device and provides a space 19, in which the light source unit 20 is disposed. Although the housing 10 generally forms the appearance of the lighting device, an additional case or component may be further provided outside the lighting device, and additional components may be further mounted when the lighting device is applied to other devices.

The housing 10 may have a shape substantially corresponding to a shape of the light source unit 20, and one side of the housing 10 is opened, such that light emitted from the light source unit 20 may travel to the outside.

As shown in FIG. 1, an overall shape of the housing 10 may have a long bar shape, in which a portion thereof in the downward direction is opened. In the illustrated exemplary embodiment, the housing 10 may have substantially a cuboid shape, and in this case, the housing 10 may include a bottom portion 11, on which the light source unit 20 is disposed, and sidewall portions 13 and 15 connected to the bottom portion 11. However, the inventive concepts are not limited thereto, and in some exemplary embodiments, the housing 10 may have a variety of shapes (e.g., a semi-cylindrical shape cut in a longitudinal direction).

The bottom portion 11 may have a rectangular shape extending in one direction. More particularly, the bottom portion 11 may have an elongated plate shape corresponding to a horizontal plane. In the illustrated exemplary embodiment, the light source unit 20 may be disposed on the bottom portion 11.

The sidewall portions 13 and 15 are connected to the bottom portion 11. The sidewall portions 13 and 15 may extend from the bottom portion 11 at various angles. For example, the sidewall portions 13 and 15 may be vertically connected to the bottom portion 11, or may be connected to the bottom portion 11 at an obtuse or acute angle.

The sidewall portions 13 and 15 may include a first sidewall portion 13 connected to a side in a lengthwise direction of the bottom portion 11, and a second sidewall portion 15 connected to a side in a widthwise direction of the bottom portion 11.

The bottom portion 11 and the sidewall portions 13 and 15 of the housing 10 may be integrally formed with each other without being separated from each other. However, the inventive concepts are not be limited thereto. In some exemplary embodiments, a portion of the housing 10 may be assembled with the other portion of the housing 10 after being provided separately. For example, the bottom portion 11 and the sidewall portion 13 of the housing 10 may be integrally formed with each other without being separated from each other, and the second sidewall portion 15 may be assembled with the bottom portion 11 and the first sidewall portion 13 after being manufactured separately.

The housing 10 may include a variety of materials. The housing 10 may include a metal material, such as aluminum or a stainless steel, without being limited thereto. The housing 10 may include other materials having a durability and capable of accommodating the light source unit 20 therein. For example, the housing 10 may include a polymer resin, and/or materials having minimal discoloration or cracking from ultraviolet light. When the housing 10 is entirely integrally formed without being separated, the housing 10 may include one material, for example, a metal material. When at least a portion of the housing 10 is not integrally formed, the housing 10 may include one material or two or more materials. For example, the bottom portion 11 and a portion of the sidewall portion of the housing 10 may include the metal material, such as aluminum, and the other portion of the sidewall portion may include the polymer resin or the like.

In some exemplary embodiments, the bottom portion 11, the first sidewall portion 13, and/or the second sidewall portion 15 may be provided with additional components, such as a through hole to withdraw a line, and a fastening structure to be coupled to the kitchen furniture. For example, the through hole may be defined through one side of the bottom portion 11, such that the line for applying power to the light source unit 20 may pass therethrough to be connected to the light source unit 20.

The light source unit 20 is accommodated in the space 19 provided by the housing 10.

Figure 3A:
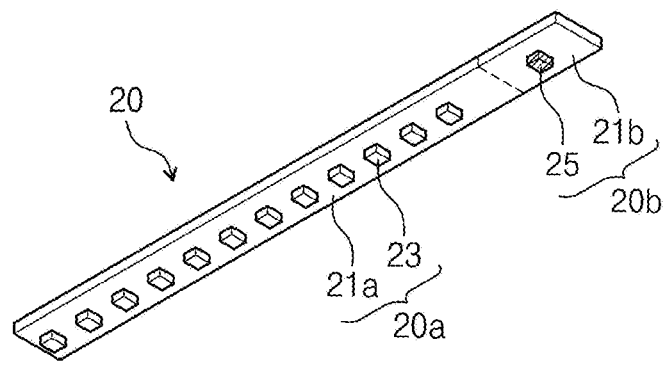
FIG. 3A and FIG. 3B are perspective views of light source units according to an exemplary embodiment.
Figure 3B:
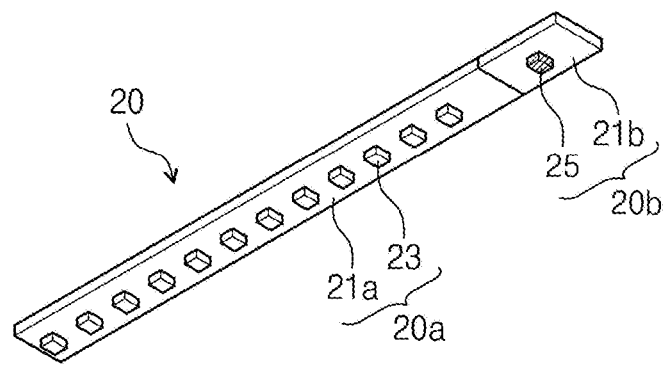

FIGS. 3A and 3B are perspective views showing light source units 20 according to exemplary embodiments.

Referring to FIGS. 3A and 3B, the light source unit 20 includes first and second light source units 20a and 20b that each emits light having different wavelength bands from each other. The first light source unit 20a emits a visible light to illuminate a predetermined area, and the second light source unit 20b disposed on the bottom portion 11 of the housing 10 emits light for sterilizing the predetermined area.

Light emitted from the first light source unit 20a may have various wavelength bands including a visible light region. According to an exemplary embodiment, light emitted from the first light source unit 20a may have a visible light wavelength band, however, in other exemplary embodiments, light may have a wavelength band other than the visible light wavelength band.

In an exemplary embodiment, the first light source unit 20a may be provided in a surface light source form and/or a point light source form. In the illustrated exemplary embodiment, the first light source unit 20a may be provided in the point light source form.

The first light source unit 20a includes a first substrate 21a and at least one first light source 23 mounted on the first substrate 21a. In the illustrated exemplary embodiment, twelve first light sources 23 are exemplarily shown.

The first substrate 21a may be provided in a plate shape. The first substrate 21a may have a shape elongated in a predetermined direction, and in this case, a lengthwise direction of the first substrate 21a may be the same as the lengthwise direction of the housing 10. However, the inventive concepts are not limited to a particular shape of the first substrate 21a, and in some exemplary embodiments, the first substrate 21a may have various shapes, on which the first light source 23 is mounted.

According to an exemplary embodiment, at least one or more first light sources 23 may be disposed on one surface of the first substrate 21a. When the first light source 23 is provided in a plural number, the first light sources 23 may be arranged in various shapes, such as being randomly arranged, being arranged to have a specific shape, being provided along one straight line, or being provided along a zigzag shape. In this case, the light sources may irradiate an increased amount of light in the downward direction.

When the first light source unit 20a includes the plural first light sources 23, the first light sources 23 may each emit light having the same wavelength band, or may each emit light having different wavelength bands from each other. For example, in an exemplary embodiment, each of the first light sources 23 may emit light having the visible light wavelength band. According to another exemplary embodiment, some light sources may emit a portion of the visible light wavelength band, and others may emit the other portion of the visible light wavelength band. When the first light sources 23 emit light having different wavelength bands from each other, the light sources may be arranged in various shapes and orders. For example, each of the first light sources 23 may emit visible lights of various colors, for example, red, green, yellow, blue, and the like, and a white light may be emitted by a combination of light having various colors emitted from the first light sources 23. As another exemplary, the white light may also be formed by applying a yellow fluorescent substance to the first light source 23 that emits a blue light. However, the wavelength band of light emitted from the light source are not limited to the above-mentioned range.

According to an exemplary embodiment, when a light emitting diode is used as the first light source 23 of the first light source unit 20a, the light emitting diode may be mounted on the first substrate 21a. The light emitting diode may be mounted on the first substrate 21a in the form of an injection-molded lead frame package capable of surface mounting, in the form of through hole mounting, in the form of a bare chip, or in the form of a flip chip. In addition, the light emitting diode may be mounted after being attached to an additional substrate 21, so as to improve heat dissipation characteristics or electrical characteristics of the light emitting diode.

A connector may further be disposed on the first substrate 21a of the first light source unit 20a to connect the first light source 23 to the line. The line (e.g., a power line) may be connected to the first light source unit 20a through the connector.

In an exemplary embodiment, the first light source unit 20a may emit light in the downward direction. As shown in figures, when the first light sources 23 are disposed on the one surface of the first substrate 21a, light may be mainly emitted to a direction vertical to the surface, on which the first light sources 23 are disposed. However, in other exemplary embodiments, the direction of light emitted from the first light source unit 20a may be variously changed.

The second light source unit 20b may include a second substrate 21b and at least one second light source 25 mounted on the second substrate 21b.

The second light source unit 20b may emit light having the sterilization function to prevent or at least suppress the growth of bacteria and the like. For example, the second light source unit 20b may emit light having an ultraviolet light wavelength band. In an exemplary embodiment, the second light source unit 20b may emit light having a wavelength band of about 100 nm to about 405 nm, which is a wavelength band capable of sterilizing microorganisms. According to exemplary embodiments, the second light source unit 20b may emit light having a wavelength band of about 100 nm to about 280 nm, may emit light having a wavelength band of about 180 nm to about 280 nm, and may emit light having a wavelength band of about 250 nm to about 260 nm. Since the ultraviolet light having the wavelength bands have a great germicidal power, when the ultraviolet light is irradiated at an intensity of about 100 μW per 1 cm², bacteria such as *Escherichia coli, Corynebacterium diphtheriae*, and *Dysentery bacillus* may be killed by about 99%. In addition, the ultraviolet light in the above wavelength bands may kill food poisoning-causing bacteria, such as Pathogenic *Escherichia coli, Staphylococcus aureus, Salmonella* Weltevreden, *S. Typhumurium, Enterococcus faecalis, Bacillus cereus, Pseudomonas aeruginosa, Vibrio parahaemolyticus, Listeria monocytogenes, Yersinia enterocolitica, Clostridium perfringens, Clostridium botulinum, Campylobacter jejuni*, or *Enterobacter sakazakii*, which causes food poisoning.

In an exemplary embodiment, when the light emitting diode is used as the second light source 25, an angle that corresponds to about 50% of the maximum amount of light emitted from the second light source 25 may be in a range of about 60 degrees to about 70 degrees, based on a line extending from a center of the second light source 25 along a direction substantially perpendicular to a light emitting surface of the second light source 25. When the angle that corresponds to about 50% of the maximum amount of light emitted from the second light source 25 is based on a substrate surface, rather than the center of the second light source 25, the angle may be in a range of about 120 degrees to about 140 degrees.

The second substrate 21b may have a plate shape. The second substrate 21b may have a shape elongated in a predetermined direction, and in this case, a lengthwise direction of the second substrate 21b may be the same as the lengthwise direction of the housing 10. However, the inventive concepts are not limited to a particular shape of the second substrate 21b, and in other exemplary embodiments, the second substrate 21b may have various shapes, on which the second light source 25 is mounted.

In an exemplary embodiment, the first substrate 21a and the second substrate 21b may be formed separately. According to another exemplary embodiment, the first substrate 21a may be provided integrally with the second substrate 21b without being separated from the second substrate 21b. In the illustrated exemplary embodiment of FIG. 3A, the first substrate 21a may be provided integrally with the second substrate 21b without being separated from the second substrate 21b, and thus, one common substrate (hereinafter, referred to as a "common substrate 21") is provided. More particularly, the first light source 23 and the second light source 25 may be disposed on the one common substrate 21 shared by the first and second light sources 23 and 25. In the illustrated exemplary embodiment of FIG. 3B, the first and second substrates 21a and 21b are provided individually.

As shown in FIGS. 3A and 3B, in the above-described exemplary embodiments, the first light source 23 and the second light source 25 may be provided on the common substrate 21 that is flat, or may be provided on the same plane rather than on the common substrate 21. As such, the first light source 23 and the second light source 25 disposed on the first and second substrates 21a and 21b are provided on substantially the same plane.

The second light source 25 is disposed on the second substrate 21b. In FIGS. 3A and 3B, one second light source 25 is illustrated, however, the inventive concepts are not be limited thereto. According to another exemplary embodiment, the second light source 25 may be provided in a plural number. When the second light source 25 is provided in a plural number, the second light sources 25 may be arranged in various shapes, such as being randomly arranged, being arranged to have a specific shape, being provided along one straight line, or being provided along a zigzag shape. In this case, the amount of light irradiated from the light sources may be increased in the downward direction.

When the second light source unit 20b includes the plural second light sources 25, the second light sources 25 may each emit light having the same wavelength band, or may each emit light having different wavelength bands from each other. For example, in an exemplary embodiment, each of the second light sources 25 may emit light having the ultraviolet light wavelength band. According to another exemplary embodiment, some light sources may emit a portion of the ultraviolet light wavelength band, and the other light sources may emit the other portion of the other wavelength bands of the ultraviolet light wavelength band. When light emitted from the second light sources 25 have different wavelength bands from each other, the light sources may be arranged in various shapes and orders. However, when the light emitting diode is used as the second light source 25 of the second light source unit 20b, the light emitting diode may be mounted on the common substrate 21.

A connector may further be disposed on the second substrate 21b of the second light source unit 20b to connect the second light source 25 to the line. The line (e.g., a power line) may be connected to the second light source unit 20b through the connector.

In the illustrated exemplary embodiment, a separate line that connects the first light source 23 and the second light source 25 may be connected to the second substrate 21b through a separate connector, however, the inventive concepts are not limited thereto. In some exemplary embodiments, for example, the first light source 23 and the second light source 25 may be connected to an external power source through one connector depending on the arrangements of the lines.

In the illustrated exemplary embodiment, the second light source unit 20b may emit light in the downward direction. As shown in the figures, when the second light source 25 is disposed on the one surface of the second substrate 21b, light may be mainly emitted to a direction vertical to the surface, on which the second light sources 25 is disposed, and the emitted light may sterilize an area in the downward direction. However, in other exemplary embodiments, the direction of light emitted from the second light source unit 20b may be variously changed.

In the illustrated exemplary embodiment, the first and/or second light source unit 20a and/or 20b may directly make contact with the bottom portion 11, however, the inventive concepts are not limited thereto. For example, the first and/or second light source unit 20a and/or 20b may not make contact with the bottom portion 11, as long as light is provided to an external area. For example, the light source unit 20 may be provided to protrude from the bottom portion 11 and the sidewall portions 13 and 15.

In the illustrated exemplary embodiment, the first light source 23 is spaced apart by a distance, at which light emitted from the second light source 25 reaches below a predetermined degree. Since light emitted from the second light source 25 is ultraviolet light, deformation of the first light source 23 may be minimized by reducing the amount of light emitted from the second light source 25 from reaching the first light source 23. The first light source 23 includes various light emitting materials and fluorescent materials, which include organic and inorganic materials. As such, when the first light source 23 is exposed to the ultraviolet light, the materials of the first light source 23 may be deformed to cause defects in the first light source 23. Accordingly, in the illustrated exemplary embodiment, the first light source 23 closest to the second light source 25 may be spaced apart from the second light source 25 at least by a distance dl based on a line extending from the center of the second light source 25 along a direction substantially perpendicular to a light emitting surface of the second light source 25, such that the first light source 23 is not disposed within an angle that corresponds to about 50% of a maximum amount of light emitted from the second light source 25.

At least about 50% or more of light emitted from the second light source 25 is emitted within the above described angle, and substantially simultaneously, at least a portion of the light amount that is less than about 50% is emitted within a predetermined angle in an area other than the above described angle. However, the light emission may be significantly reduced depending on the distance from the second light source 25. In the illustrated exemplary embodiment, to prevent the deformation of the first light source 23, the first light source 23 and the second light source 25 adjacent to the first light source 23 are spaced apart from each other, such that light of about 50% or less of the maximum amount of light emitted from the second light source 25 reaches the first light source 23. Hereinafter, an area having an angle corresponding to about 50% of the maximum amount of light based on the line extending from the center of the second light source 25 along a direction substantially perpendicular to a light emitting surface of the second light source 25 will be referred to as a "first area", and an area outside the first area, that is, the area having an angle corresponding to less than about 50% of the maximum amount of the light will be referred to as a "second area". As such, the first light source 23 is disposed in the second area.

Referring back to FIGS. 1 and 2, the cover unit 30 is disposed in the opened portion of the housing 10.

The cover unit 30 is coupled to the sidewall portions 13 and 15 to face the bottom portion 11, and covers at least a portion of the light source unit 20. In the illustrated exemplary embodiment, the light source unit 20 including the first light source unit 20a and the second light source unit 20b is disposed in the space of the housing 10, and the cover unit 30 covers both the first and second light source units 20a and 20b.

The cover unit 30 has a shape similar to the bottom portion 11 of the housing 10. More particularly, similarly to the bottom portion 11, the cover unit 30 may have a rectangular shape extending in one direction, and may have an elongated plate shape corresponding to a horizontal plane. The cover unit 30 may be spaced apart from the bottom portion 11 of the housing 10 by a distance corresponding to a height of the sidewall portions.

The cover unit 30 may have a size similar to or slightly less than that of the bottom portion 11, and may be coupled to at least one of the first sidewall portion 13 and the second sidewall portion 15 of the housing 10. In the illustrated exemplary embodiment, an insertion groove into which the cover unit 30 is to be inserted may be defined in an inner side of the first sidewall portion 13, and the cover unit 30 may be slid-coupled to the first sidewall portion 13 along the insertion groove. However, the coupling structure between the first and second sidewall portions 13 and 15 of the housing 10 and the cover unit 30 is not limited thereto, and the first and second sidewall portions 13 and 15 of the housing 10 and the cover unit 30 may be coupled to each other in various structures, e.g., a hook coupling structure. The shape or position of the cover unit 30 may be modified in various ways.

FIGS. 1 and 2 show that the cover unit 30 is formed as a single layer plate, however, the inventive concepts are not limited thereto. In some exemplary embodiments, the cover unit 30 may further include various functional films or members. For example, a diffusion member that diffuses light emitted from the first light source unit 20a and/or the second light source unit 20b may be disposed on at least one surface of both surfaces of the cover unit 30. The diffusion member may be formed as a film on at least one surface of both surfaces of the cover unit 30, or may be laminated after being manufactured as a separate film. When the diffusion member is formed as a film, various dispersants may be included in the film to disperse light, and when the diffusion member is laminated after being manufactured as a separate film, a surface of the film may be provided with haze or the like for diffusion.

The cover unit 30 may be transparent or at least semi-transparent, so as to protect the first and second light sources 23 and 25 and substantially simultaneously transmit light emitted from the first and second light source units 23 and 25. In particular, the cover unit 30 may include a material, in which defects, such as deformation, yellowing, and cracks, due to the ultraviolet light emitted from the second light source 25 may not occur or are minimized. That is, the material of the cover unit 30 is not particularly limited, as long as the function described above is satisfied. For example, the cover unit 30 may include quartz or a polymer organic material. The polymer organic material may be selected in consideration of wavelengths of light emitted from each of the first and second light sources 23 and 25, since the wavelengths that are absorbed/transmitted vary depending on a type of monomer, a molding method, and conditions. For example, a polymer resin, such as poly (methylmethacrylate) (PMMA), polycarbonate (PC), polyvinylalcohol (PVA), polypropylene (PP), and low-density polyethylene (PE) absorb little ultraviolet light, while a polymer resin such as polyester may absorb the ultraviolet light. In consideration of the absorption wavelength, the cover unit 30 may include a material that substantially does not absorb the ultraviolet light.

In the lighting device having the above-described structure according to an exemplary embodiment, the deformation of the first light source 23 due to the ultraviolet light emitted from the second light source 25 may be minimized, and thus, the reliability of the lighting device may be improved. More particularly, when the light emitting diode is used as the first light source 23, the light emitting materials in the first light source 23 may be prevented from being deformed due to the ultraviolet light.

Figure 4:
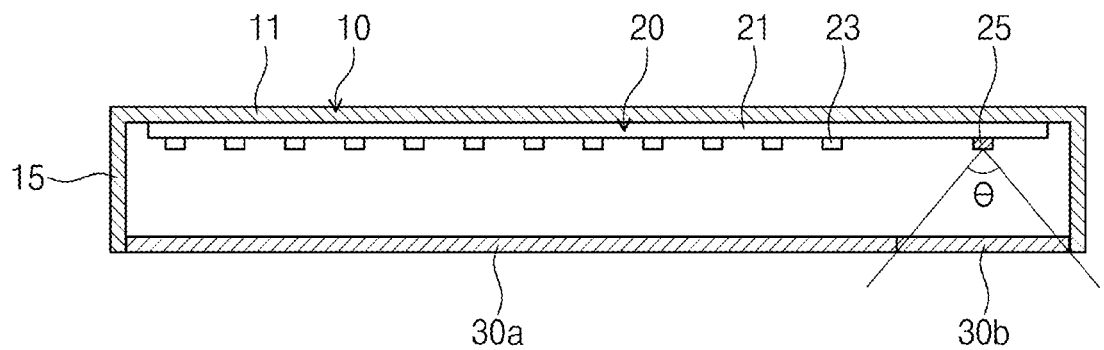
FIG. 4 is a cross-sectional view of a lighting device according to an exemplary embodiment.

FIG. 4 shows a lighting device, to which different cover units 30 are applied to correspond to emitted light according to an exemplary embodiment. In the following exemplary embodiments, different features from the above-described exemplary embodiments will be mainly described in order to avoid redundancy.

Referring to FIG. 4, the cover unit 30 may include a first sub-cover 30a and a second sub-cover 30b. The first sub-cover 30a and the second sub-cover 30b may be formed integrally with each other, or may be formed separately from each other. The first sub-cover 30a and the second sub-cover 30b may include a material that transmits light emitted from the light source unit 20 in consideration of light emitted from the corresponding light source unit 20.

The first sub-cover 30a is disposed at a position corresponding to the first light source unit 20a. Since light provided from the first light source unit 20a is the visible light, the first sub-cover 30a may include a material that transmits the visible light. The first sub-cover 30a may include, for example, glass, quartz, or polymer resin. As the polymer resin, polystyrene, polyvinyl alcohol, polymethyl methacrylate, polyethersulfone, polyacrylate, polyetherimide, polyethylene, polyethylene naphthalate, polyethylene terephthalate, polyphenylene sulfide, polyarylate, polyimide, polycarbonate, triacetate cellulose, cellulose acetate propionate, and polypropylene may be used.

The second sub-cover 30b is disposed at a position corresponding to the second light source unit 20b. The area in which the second light source unit 20b faces is an area corresponding to the angle within which light emitted from the first light source unit 20a is greater than a predetermined amount of light. In this case, the predetermined amount of light may refer to a light amount that may cause the deformation of the cover unit 30 by the ultraviolet light.

Since light provided from the second light source unit 20b is the ultraviolet light, the second sub-cover 30b may include a material that transmits the ultraviolet light. For example, the second sub-cover 30b may include quartz and a polymer resin, such as, poly(methylmethacrylate) (PMMA), polycarbonate (PC), polyvinylalcohol (PVA), polypropylene (PP), low-density polyethylene (PE), as the material that transmits the ultraviolet light, without being limited thereto.

According to an exemplary embodiment, the cover unit 30 is formed using a material having high transmittance with respect to the visible light in an area where the visible light is mainly transmitted, and the cover unit 30 is formed using a material having high transmittance with respect to the ultraviolet light in an area where the ultraviolet light is mainly transmitted, thereby maintaining the high transmittance with respect to the visible light and the ultraviolet light, and preventing the deformation and cracks of the cover unit 30 by the ultraviolet light. Furthermore, since ultraviolet light-transmitting materials that are generally more expensive are less used, costs of manufacturing the lighting device may be reduced.

In the lighting device according to an exemplary embodiment, the position of the second light source 25 may be variously changed to prevent the deformation of the first light source 23 due to the ultraviolet light emitted from the second light source 25.

FIGS. 5 to 9 are cross-sectional views of lighting devices according to exemplary embodiments.

Figure 5:
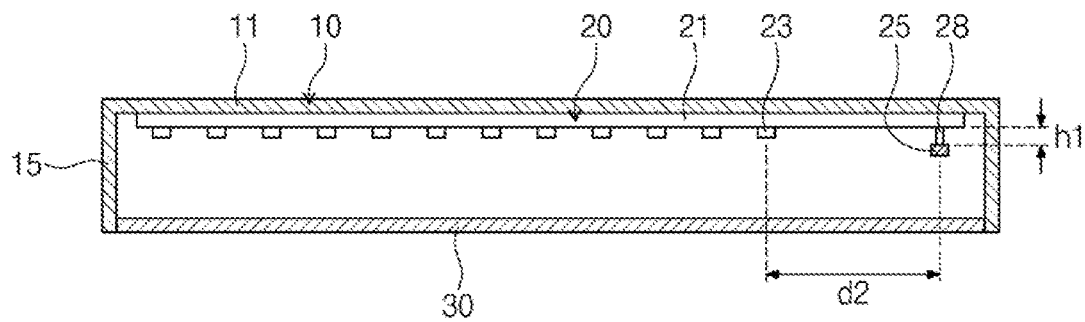
FIG. 5, FIG. 6, FIG. 7, FIG. 8, and FIG. 9 are cross-sectional views of lighting devices according to exemplary embodiments.

Referring to FIG. 5, a first light source 23 and a second light source 25 may be provided to have different heights from a bottom portion 11 of a housing 10. In particular, the first light source 23 and the second light source 25 may be disposed on different planes from each other.

In the illustrated exemplary embodiment, a first substrate 21a of a first light source unit 20a and a second substrate 21b of a second light source unit 20b may be shared in the form of a common substrate 21. However, the first light source 23 of the first light source unit 20a is disposed directly on the common substrate 21, and the second light source 25 of the second light source unit 20b is disposed at a position spaced apart from the common substrate 21 by a predetermined height. A protrusion 28 protruded from the common substrate 21 may be disposed between the second light source 25 and the common substrate 21. When a height of the protrusion 28 is referred to as a "first height h1", the second light source 25 and the common substrate 21 are spaced apart from each other by the first height h1.

Since light emitted from each of the first and second light sources 23 and 25 travels in the downward direction, and the second light source 25 emits light to the downward direction while being spaced apart from the common substrate 21 by the first height h1, light emitted from the second light source 25 and traveling toward the first light source 23 may be greatly reduced. Accordingly, the first light source 23 may be prevented from being deformed due to the ultraviolet light emitted from the second light source 25.

Figure 6:
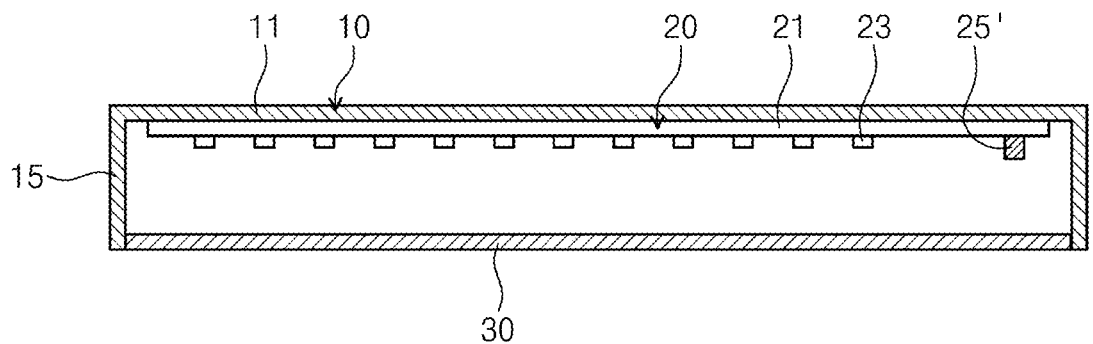

FIG. 6 is a cross-sectional view of a lighting device according to another exemplary embodiment.

Referring to FIG. 6, similarly to FIG. 5, a first light source 23 and a second light source 25 may be provided to have different heights from a bottom portion 11 of a housing 10. As such, the first light source 23 and the second light source 25 may be disposed on different planes from each other. However, different from the structure shown in FIG. 5, in the illustrated exemplary embodiment, packages for the first light source 23 and the second light source 25 have different heights. In particular, the first light source 23 and the second light source 25 may each be provided in the form of package, in which a light emitting diode is mounted on a front surface. In this case, a height of an emission point of the first light source 23 and the second light source 25 may be controlled by adjusting the height of the package. In FIG. 6, the height of the package of the second light source 25 is greater than the height of the package of the first light source 23. As such, since light is emitted downward from the second light source 25 while the second light source 25 is further spaced apart from a substrate 21 than the first light source 23, light emitted from the second light source 25 and traveling toward the first light source 23 may be reduced. Accordingly, the first light source 23 may be prevented from being deformed by the ultraviolet light emitted from the second light source 25.

Figure 7:
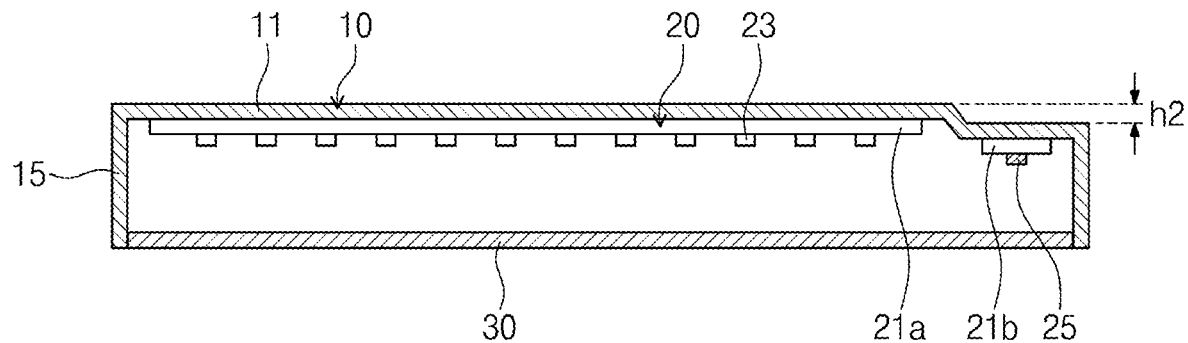

FIG. 7 is a cross-sectional view of a lighting device according to another exemplary embodiment.

Referring to FIG. 7, similarly to FIG. 5, a first light source 23 and a second light source 25 may be provided to have different heights from a bottom portion 11 of a housing 10. As such, the first light source 23 and the second light source 25 may be disposed on different planes from each other. However, different from the structure shown in FIG. 5, a shape of the housing 10 is partially different from that of a substrate 21.

According to the illustrated exemplary embodiment, the housing 10 may include a stepped portion protruding downward to correspond to an area, in which the second light source 25 is disposed. The stepped portion is a portion that protrudes downward by a second height h2 from the other area of a bottom portion 11 of the housing 10, where the first light source 23 is disposed.

In the illustrated exemplary embodiment, a first light source unit 20a is disposed on the bottom portion 11 except for the stepped portion. More particularly, a first substrate 21a and the first light source 23 are disposed on the bottom portion 11 except for the stepped portion. A second light source unit 20b is disposed on the stepped portion. In particular, a second substrate 21b and the second light source 25 are disposed on the stepped portion.

In the illustrated exemplary embodiment, since light emitted from the first and second light sources 23 and 24 travels in the downward direction, and light is emitted downward from the second light source 25 while the second light source 25 is spaced apart by the height h2, light emitted from the second light source 25 and traveling toward the first light source 23 may be greatly reduced. Accordingly, the first light source 23 may be prevented from being deformed by the ultraviolet light emitted from the second light source 25.

In the illustrated exemplary embodiment, although not shown in figures, each of the first light source unit 20a and the second light source unit 20b may be connected to a power line.

In addition, the number of the first light sources 23 of the first light source unit 20a, the number of the second light sources 25 of the second light source unit 20b, and positions at which the first light sources 23 and the second light sources 25 are disposed may be changed in various ways.

Figure 8:
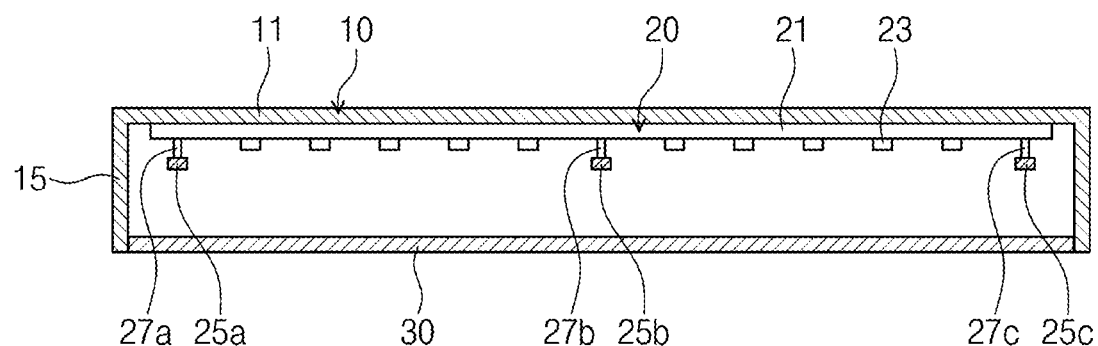

FIG. 8 is a cross-sectional view of a lighting device according to an exemplary embodiment.

Referring to FIG. 8, in the illustrated exemplary embodiment, the number of the first light sources 23 is ten, which is different from the above-described exemplary embodiments. In addition, the second light sources 25 are disposed at both ends and an intermediate point in a lengthwise direction. In the illustrated exemplary embodiment, the number and position of the second light sources 25 may be changed in various ways by taking into account objects to be sterilized.

Figure 9:
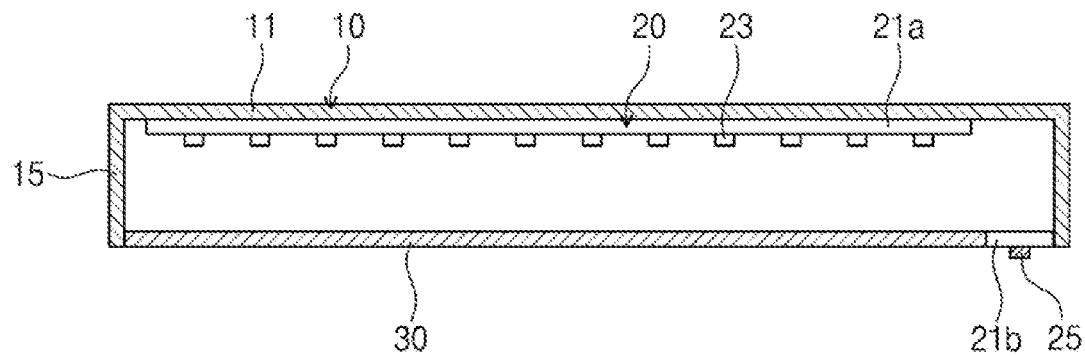

FIG. 9 is a cross-sectional view showing a lighting device according to an exemplary embodiment.

Referring to FIG. 9, a first light source unit 20a and a second light source unit 20b may be provided to have different heights from a bottom portion 11 of a housing 10. In particular, the first light source 23 and the second light source 25 may be disposed on different planes from each other.

In the illustrated exemplary embodiment, the second light source unit 20b may be disposed on a sidewall portion of the housing 10, rather than being disposed on a bottom portion 11 of the housing 10. In particular, a second substrate 21b of the second light source unit 20b may be coupled to an end portion of the first and/or second sidewall portion 15 of the housing 10, and the second light source 25 may be disposed on the second substrate 21b.

The second light source unit 20b may be mounted in various forms using various coupling members, such as being inserted and coupled to the first and/or second sidewall portion 15, being coupled to the first and/or second sidewall portion 15 using a hook, or being screw coupled to the first and/or second sidewall portion 15.

In this case, the cover unit 30 includes an opening in an area where the second light source unit 20b is to be provided. Accordingly, the cover unit 30 covers only the first light source unit 20a to face the first light source unit 20a, and does not cover the second light source unit 20b. The second light source unit 20b may be exposed to the outside through the opening. The second light source unit 20b is disposed at substantially the same height as the cover unit 30 from the bottom portion 11 of the housing 10. In the illustrated exemplary embodiment, the second substrate 21b of the second light source unit 20b may be disposed at substantially the same height as the cover unit 30.

In the illustrated exemplary embodiment, since the second light source unit 20b is not covered by the cover unit 30, an additional component may be further provided to protect the second light source 25.

Figure 10:
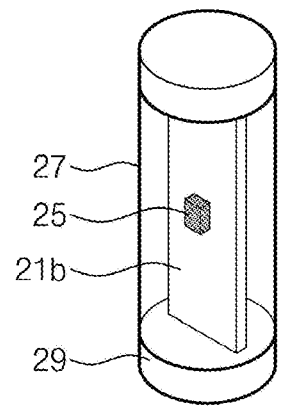
FIG. 10 is a perspective view of a second light source unit according to an exemplary embodiment.

FIG. 10 is a perspective view showing a shape of a second light source unit 20b according to an exemplary embodiment.

Referring to FIG. 10, the second light source unit 20b may include a protective tube 27 protecting a second substrate 21b and a second light source 25 of the second light source unit 20b. The protective tube 27 is formed of a transparent insulating material, protects the second light source 25 and the second substrate 21b, and transmits light emitted from the second light source 25. The protective tube 27 may include various materials, as long as the above-described functions are satisfied, and the materials thereof are not particularly limited. The protective tube 27 may include a material that transmits the ultraviolet light, e.g., quartz or a polymer organic material.

The protective tube 27 may have a cylindrical shape, in which both sides are opened. Caps 29 may be disposed at the opened both ends to withdraw a line. At least one of the caps 29 on both sides allows the second substrate 21b and the second light source 25 to be stably placed in the protective tube 27, and may be connected to a power line to provide a power to the second light source 25.

In an exemplary embodiment, as a coupling member for coupling the second light source unit 20b to the sidewall portion, both caps 29 may be further provided with a wing-shaped coupling member protruding outwardly. The wing-shaped coupling member may be provided with a screw hole or an insertion hole, and may be coupled to the housing 10 using a screw or a protrusion 27 inserted into the insertion hole.

According to the illustrated exemplary embodiment, a cover unit 30 does not cover the second light source unit 20b. Accordingly, light having the ultraviolet light wavelength band and emitted from the second light source unit 20b is not transmitted through the cover unit 30, and thus, the deformation of the cover unit 30, such as yellowing and crack due to the ultraviolet light, may be prevented.

Figure 11A:
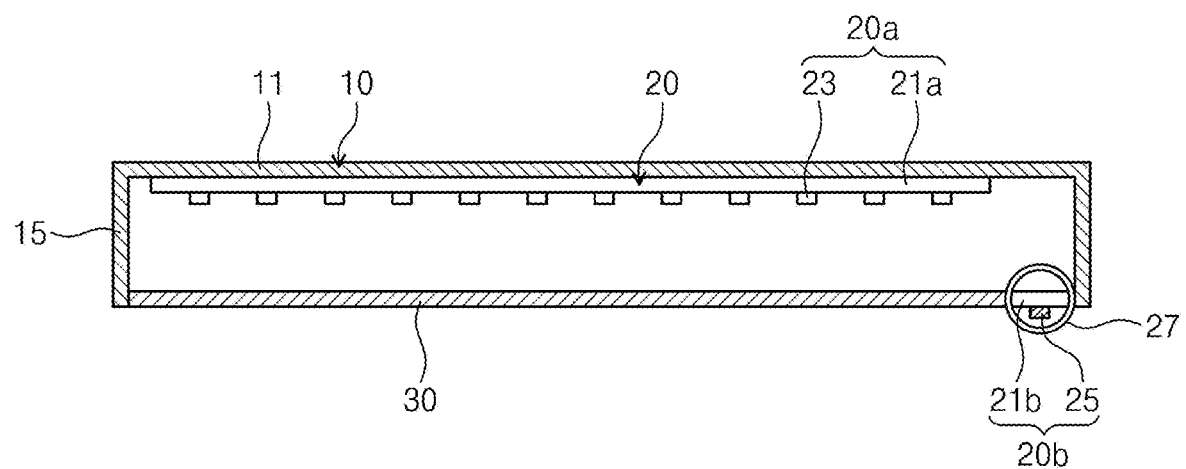
FIG. 11A and FIG. 11B are cross-sectional views of a lighting device with a light source of FIG. 10 according to an exemplary embodiment.
Figure 11B:
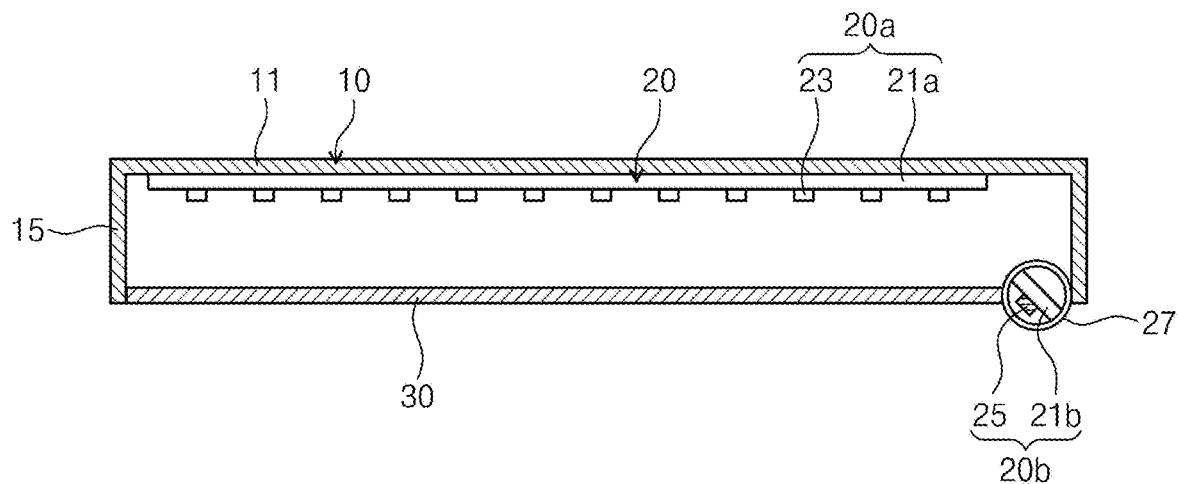

FIGS. 11A and 11B are cross-sectional views of a lighting device with the light source shown in FIG. 10 according to an exemplary embodiment.

Referring to FIGS. 11A and 11B, a second light source unit 20b of the lighting device according to an exemplary embodiment may rotate to increase the sterilization efficiency by irradiating the ultraviolet light to various areas. In particular, referring to FIG. 11A, light emitted from the second light source unit 20b may be provided in the downward direction in the same manner as in a first light source unit 20a. Referring to FIG. 11B, a second light source unit 20b rotates at a predetermined angle, and thus, light emitted from the second light source unit 20b may be provided in a direction, e.g., in a downward direction on one side, different from that of a first light source unit 20a. The rotation angle of the second light source unit 20b may be changed in various ways depending on the positions of the object to be sterilized.

Although not shown in the figures, a rotation unit may be mounted on the second light source unit 20b to control a light emission direction of the lighting device. As the rotation unit, a manual rotation unit that allows the user to directly adjust the light emission direction of the lighting device, or an automatic rotation unit that automatically adjusts the light emission direction may be provided. In this manner, the light emission direction of light from the second light source unit 20b may be easily changed. In this case, since the ultraviolet light is irradiated over a wide area, the sterilization area may be increased. In the illustrated exemplary embodiment, the light emission direction of the second light source unit 20b is changed along the lengthwise direction of the housing 10, however, the inventive concepts are not limited thereto. In other exemplary embodiments, the light emission direction of the second light source unit 20b may be changed to another direction depending on the arrangement direction of the second light source unit 20b, for example, in the widthwise direction of the housing 10.

In the above-described exemplary embodiments, the second light source unit 20b is illustrated as being fixedly disposed at a predetermined position, however, the position of the second light source unit 20b may be variously changed in other exemplary embodiments. More particularly, the position of the second light source unit 20b may be changed in various ways by the user.

Figure 12:
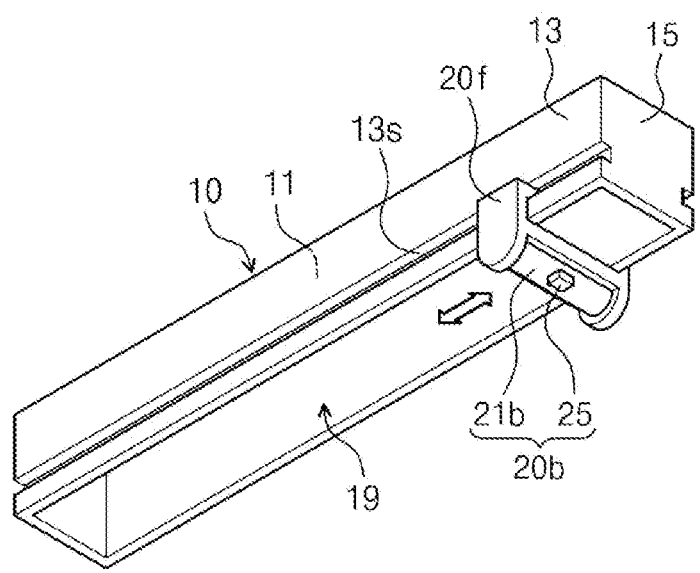
FIG. 12 is a perspective view of a lighting device according to an exemplary embodiment.

FIG. 12 is a perspective view of a lighting device according to an exemplary embodiment. In FIG. 12, a housing 10 and a second light source unit 20b are exemplarily shown, and some components thereof are not illustrated.

Referring to FIG. 12, the lighting device according to the illustrated exemplary embodiment may include a coupling unit that is attachable and detachable to change a coupling position of the second light source unit 20b. The coupling unit may be provided in at least one of the housing 10 and the second light source unit 20b, and the type or shape of the coupling unit is not particularly limited, as long as the second light source unit 20b is coupled to a predetermined position of the housing 10. For example, in the illustrated exemplary embodiment, a coupling unit 20f may be mounted on the second light source unit 20b to allow the second light source unit 20b to be coupled to the housing 10. The coupling unit 20f may be provided in the form of hook protruding toward the housing 10 to fix the second light source unit 20b to the housing 10. As such, a slide groove 13s, through which the hook is inserted and moved, may be formed in a sidewall portion 13 of the housing 10. Accordingly, the second light source unit 20b may be coupled to the housing 10 by the coupling unit 20f, and may move along the slide groove 13s in the lengthwise direction of the housing 10.

Although not shown in figures, as the coupling unit 20f of the second light source unit 20b, a manual coupling unit that allows the user to directly adjust the position of the second light source unit 20b, or an automatic coupling unit that automatically adjusts the position of the second light source unit 20b may be provided. In this manner, the light emission position of light from the second light source unit 20b may be easily changed. In this case, since the ultraviolet light is irradiated over a wide area, the sterilization area may be increased. In the illustrated exemplary embodiment, the light emission position of the second light source unit 20b is described as being changed along the lengthwise direction of the housing 10, however, the inventive concepts are not limited thereto. In some exemplary embodiments, the light emission position may be changed to another direction depending on the arrangement direction of the second light source unit 20b, for example, in the widthwise direction of the housing 10.

In the above-described exemplary embodiments, the hook that is coupled to the slide groove is described as the attachable and detachable coupling unit, however, the coupling unit is not limited to the hook. For example, in some exemplary embodiments, the coupling unit may be provided in various forms as long as the coupling unit may be coupled to components in the lighting device while varying its position.

The lighting device according to an exemplary embodiment further include various types of sensors, and may further include a controller for controlling on/off of the lighting device in accordance with information sensed by the sensor.

Figure 13:
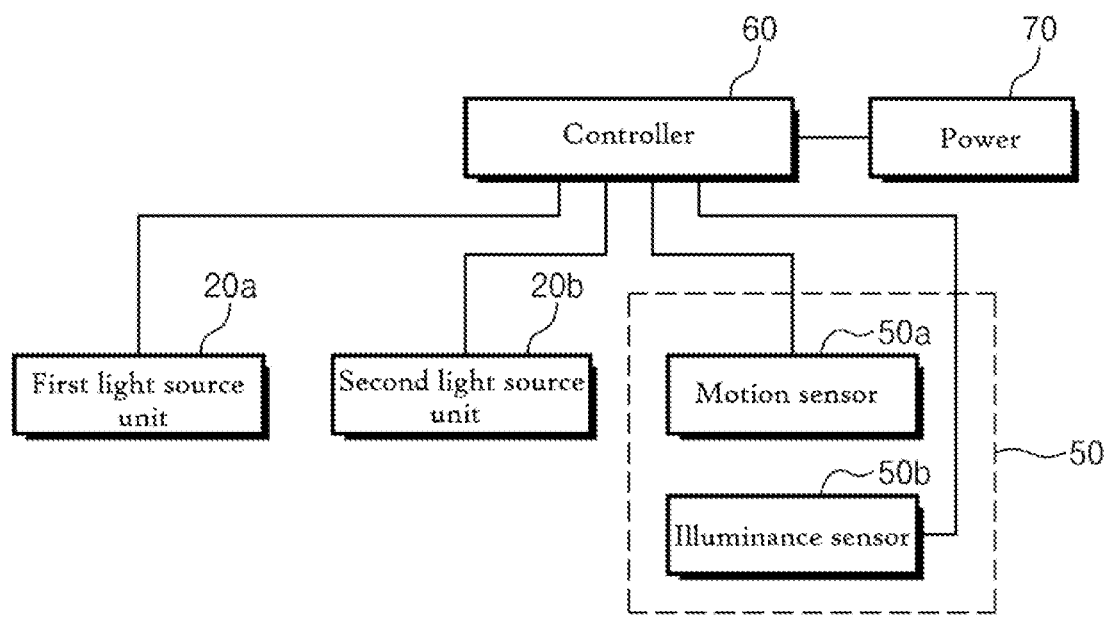
FIG. 13 is a block diagram of a lighting device according to an exemplary embodiment.

FIG. 13 is a block diagram of a lighting device according to an exemplary embodiment. Referring to FIG. 13, the lighting device according to an exemplary embodiment may include a first light source unit 20a emitting the visible light, a second light source unit 20b emitting the ultraviolet light, a sensor 50 sensing the user's motion or illuminance of external light, and a controller 60. The controller 60 is connected to each of the first light source unit 20a, the second light source unit 20b, and the sensor 50, and controls the first light source unit 20a, the second light source unit 20b, and the sensor 50. The controller 60 is connected to a power, and the power is provided to the first light source unit 20a, the second light source unit 20b, and the sensor 50.

The controller 60 may be a motion sensor 50a that senses the user's motion and/or an illumination sensor 50b that senses the illuminance of external light.

The controller 60 drives on/off of the power of a first light source 23 and a second light source 25 according to a sensing result of at least one of the illumination sensor 50b and the motion sensor 50a.

The motion sensor 50a may sense whether the user is active. When the user's activity is sensed by the motion sensor 50a, the first light source unit 20a may be turned on, and the second light source unit 20b may be turned off. In contrast, when the user's activity is not sensed by the motion sensor 50a, the first light source unit 20a may be turned off, and the second light source unit 20b may be turned on. As another example, when it is sensed through the motion sensor 50a that a distance between the lighting device and the user reaches a predetermined limit approach distance, the second light source unit 20b may be turned off.

The illumination sensor 50b may sense the illuminance of ambient external light. The controller 60 may preset at least one illuminance range of the ambient light, and then, may turn on/off the first and second light source units 20a and 20b, or may control an amount of light emitted from the first and second light source units 20a and 20b according to the sensed illuminance range of the ambient light.

In an exemplary embodiment, the illumination sensor 50b may sense the illuminance of external light, without being limited thereto. In some exemplary embodiments, the illumination sensor 50b may sense illuminance of light from the first light source 23 or the light from the second light source 25. In this case, when the illuminance of light emitted from the first light source 23 or the second light source 25 is equal to or smaller than a predetermined range, the controller 60 may operate a separate alarm to notify that the first light source 23 or the second light source 25 is in need to be replaced.

As described above, the lighting device according to the exemplary embodiments may be used in various ways in accordance with whether the user is active or the amount of external light, and thus, power consumption may be reduced.

The above-described exemplary embodiments may be combined with each other in various ways. For example, the second light source may be provided on the protrusion at the one side in the lengthwise direction of the lighting device, and may be provided on the stepped portion at the other side in the lengthwise direction of the lighting device. In addition, as the position at which the second light source is disposed is changed, the first sub-cover and the second sub-cover may be changed in various forms.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A lighting device comprising:
at least one first light source configured to emit a visible light through a first light emitting surface;
at least one second light source spaced apart from the first light source and configured to emit light having a wavelength for sterilization through a second light emitting surface; and
a housing enclosing the first light source and the second light source in one common area,
wherein the first and second light emitting surfaces face substantially the same direction, and
wherein the first light source is disposed outside an area having an angle corresponding to about 50% of a maximum amount of light emitted from the second light source based on a line extending from a center of the second light source along a direction substantially perpendicular to the second light emitting surface of the second light source.

2. The lighting device of claim 1, further comprising a first substrate on which the first light source is mounted and a second substrate on which the second light source is mounted.

3. The lighting device of claim 2, wherein the first substrate and the second substrate are disposed on different planes from each other.

4. The lighting device of claim 2, wherein the first substrate and the second substrate are disposed on the same plane as each other.

5. The lighting device of claim 4, wherein the first substrate and the second substrate are integrally formed without being spaced apart from each other.

6. The lighting device of claim 1, wherein the housing comprises:
a bottom portion on which the first light source is disposed; and
a sidewall portion connected to the bottom portion.

7. The lighting device of claim 6, wherein the first light source and the second light source are disposed at different heights from the bottom portion.

8. The lighting device of claim 7, wherein the height of the first light source from a first substrate on which the first light source is mounted is lower than the height of the second light source from the first substrate.

9. The lighting device of claim 7, wherein the second light source is disposed on at least one of the bottom portion and the sidewall portion.

10. The lighting device of claim 7, further comprising a cover unit that is coupled to the sidewall portion to face the bottom portion and covers the first light source.

11. The lighting device of claim 10, wherein the cover unit comprises a diffusion member to diffuse the light.

12. The lighting device of claim 11, wherein the cover unit comprises at least one of quartz, polymethylmethacrylate, polycarbonate, polyvinylalcohol, polypropylene, and low-density polyethylene.

13. The lighting device of claim 10, wherein the cover unit covers the second light source.

14. The lighting device of claim 10, wherein the cover unit includes an opening defined in an area, in which the second light source is disposed, and the second light source is exposed to an outside through the opening.

15. The lighting device of claim 14, wherein the cover unit and a second substrate on which the second light source is mounted are disposed on the same plane as each other.

16. The lighting device of claim 1, wherein the second light source is rotatable.

17. The lighting device of claim 1, further comprising at least one of an illuminance sensor and a motion sensor which are disposed at one side of the housing.

18. The lighting device of claim 17, further comprising a controller configured to drive a power of the first light source and the second light source, and connected to at least one of the illuminance sensor and the motion sensor,
wherein the controller drives the power of the first light source and the second light source depending on a sensing result by at least one of the illuminance sensor and the motion sensor.

19. The lighting device of claim 18, wherein the controller is configured to turn off the second light source when the motion sensor senses that a distance between the lighting device and a user reaches a predetermined limit approach distance.

20. The lighting device of claim 1, wherein at least one of the first light source and the second light source is provided in plural.

21. The lighting device of claim 20, wherein the second light source is provided in plural, and at least one of the second light sources is configured to emit light having different wavelength from that emitted from the remaining second light sources.

22. The lighting device of claim 1, wherein the lighting device is mounted on a kitchen furniture.

23. A visible light lighting device coupled to a second light source that is configured to emit light having a wavelength for sterilization, comprising:
at least one first light source configured to emit a visible light; and
a housing at which the first light source is disposed,
wherein the first light source is disposed outside an area having an angle corresponding to about 50% of a maximum amount of light emitted from the second light source based on a line extending from a center of the second light source along a direction substantially perpendicular to a light emitting surface of the second light source,
wherein the second light source is rotatably coupled to the housing.

24. A light source coupled to a visible light lighting device including a first light source configured to emit a visible light, and a housing at which the first light source is disposed, comprising:
a coupling unit detachably coupled to the housing and configured to slide along a longitudinal direction of the housing,
wherein the light source is mounted on the coupling unit, the light source being configured to emit light having a wavelength for sterilization, and wherein the light source and the first light source are disposed on different planes from each other.

* * * * *